United States Patent
Hamlin et al.

(10) Patent No.: US 9,345,563 B2
(45) Date of Patent: May 24, 2016

(54) IMPLANTABLE MESH PROSTHESES AND METHOD OF MANUFACTURING SAME

(71) Applicant: C. R. Bard, Inc., Murray Hill, NJ (US)

(72) Inventors: Tami L. Hamlin, Exeter, RI (US); Shekhar D. Nimkar, Swampscott, MA (US)

(73) Assignee: C.R. Bard, Inc., Murray Hill, NJ (US)

(*) Notice: Subject to any disclaimer, the term of this patent is extended or adjusted under 35 U.S.C. 154(b) by 115 days.

(21) Appl. No.: 14/037,569

(22) Filed: Sep. 26, 2013

(65) Prior Publication Data

US 2014/0025096 A1 Jan. 23, 2014

Related U.S. Application Data

(62) Division of application No. 13/153,837, filed on Jun. 6, 2011, now Pat. No. 8,551,125.

(51) Int. Cl.
*A61F 2/00* (2006.01)

(52) U.S. Cl.
CPC ....... *A61F 2/0063* (2013.01); *A61F 2002/0068* (2013.01); *Y10T 83/04* (2015.04)

(58) Field of Classification Search
CPC ................. A61F 2/0063; A61F 2002/0068
USPC ............. 600/37; 606/151, 200; 623/23.72
See application file for complete search history.

(56) References Cited

U.S. PATENT DOCUMENTS

| | | |
|---|---|---|
| 5,356,432 A | 10/1994 | Rutkow et al. |
| 5,716,408 A | 2/1998 | Eldridge et al. |
| 6,616,685 B2 | 9/2003 | Rousseau |
| 6,726,696 B1 | 4/2004 | Houser et al. |
| 6,783,554 B2 | 8/2004 | Amara et al. |
| 2002/0188317 A1 | 12/2002 | Rousseau |
| 2003/0181988 A1 | 9/2003 | Rousseau |
| 2005/0165447 A1* | 7/2005 | Crawley et al. ............... 606/228 |
| 2008/0004657 A1* | 1/2008 | Obermiller et al. .......... 606/213 |
| 2009/0192530 A1 | 7/2009 | Adzich et al. |

(Continued)

FOREIGN PATENT DOCUMENTS

EP    0 614 650 A2    9/1994

OTHER PUBLICATIONS

Millikan et al., "A Prospective Study of the Mesh-Plug Hernioplasty," The American Surgeon, vol. 67, No. 3, pp. 285-289 (Mar. 2001).

(Continued)

*Primary Examiner* — Alexander Orkin
(74) *Attorney, Agent, or Firm* — Saul Ewing LLP

(57) ABSTRACT

Implantable prostheses for reinforcing and repairing defects in a muscular or tissue wall and a method for fabricating the prostheses that minimizes wasted mesh material and reduces the labor and time required for fabrication. The prosthesis may include a plug body formed of surgical mesh material having a closed end, a larger open end, and a cavity extending therebetween, and a filler body formed of the surgical mesh material comprising a plurality of petals extending radially outwardly from and spaced laterally about a common base disposed in the plug body with the common base attached to the closed end of the plug body. The plug bodies are cut as circular pieces, and the filler bodies are cut as hour-glass shaped pieces from the same sheet of material so as to leave virtually no wasted mesh material. The filler pieces may be attached to the plug body piece by welding.

20 Claims, 14 Drawing Sheets

(56) References Cited

U.S. PATENT DOCUMENTS

2010/0081866 A1* 4/2010 Goddard et al. ............... 600/37
2011/0118851 A1   5/2011 Eldridge et al.
2011/0178538 A1* 7/2011 Cook ........................... 606/151
2013/0138144 A1* 5/2013 Yribarren ..................... 606/213

OTHER PUBLICATIONS

International Preliminary Report on Patentability, dated Dec. 10, 2013, issued in corresponding International Application No. PCT/US2012/041010.

* cited by examiner

IMPLANTABLE MESH PROSTHESES AND METHOD OF MANUFACTURING SAME

CROSS-REFERENCE TO RELATED APPLICATIONS

This application is a division of U.S. application Ser. No. 13/153,837, filed Jun. 6, 2011, the entire contents of which is fully incorporated herein by reference.

FIELD OF INVENTION

The present invention relates to implantable mesh prostheses and to a method of manufacturing the same.

BACKGROUND OF THE INVENTION

Various prosthetic mesh materials have been proposed to reinforce the abdominal wall and to close abdominal wall defects. It has been known to fold a sheet of surgical mesh fabric into the multilayer cone configuration and then to insert the mesh plug into a hernia defect to occlude the void. One example of a mesh plug for occluding voids in tissue walls caused by herniation and the like is the Perfix® Plug commercially available from C.R. Bard, Inc. of Murray Hill, N.J., USA.

These types of plugs often are formed of a plurality of layers of mesh material that are sewn together in order to give the plug suitable structural rigidity and bulk. U.S. Pat. No. 5,356,432, which is incorporated herein fully by reference, discloses one such exemplary plug comprised of three layers of mesh material and a method of repairing muscle or tissue wall defects using such a plug. FIG. 1 herein is an exploded perspective view of one exemplary plug 10 disclosed in that patent. As can be seen, the plug comprises three layers of material 12, 14, and 16. Plug layer 12 is composed of a generally circular piece of a mesh fabric folded into a conical plug shape and bearing a plurality of pleats. Layers 14 and 16 are inner filler layers that, when the plug is assembled, are disposed inside of the outer, plug layer 12 and attached at their bases (i.e., their geometric centers) 30 to the center (or tip) 20 of outer layer 12. The circular outer plug layer 12 provides a continuous mesh piece to effectively plug the hole, while each of layers 14 and 16 provides structural rigidity and bulk to the overall prosthesis 10.

With reference to FIG. 2, layers 14 and 16 typically are formed by cutting out a circular piece 31 of the mesh material similar in size to that of the plug body 12 and then cutting out pie-shaped wedges (not shown) radially around the circular piece 31 so as to leave a plurality of petals 28 surrounding a central base 30.

Typically, the mesh material for fabricating such plugs is supplied in rectangular sheets. Accordingly, in order to cut out the circular outer layer 12 and the two filler layers 14 and 16, a significant amount of the original rectangular sheet of material is discarded, e.g., the pie-shaped pieces cut out of the originally circular filler pieces as well as the areas between all of the circular pieces.

The hernia plug industry is generally moving toward the use of more expensive mesh materials with superior qualities, such that the cost of the mesh material is becoming a more significant factor in the overall cost of the prostheses.

SUMMARY OF THE INVENTION

The present invention provides an implantable prosthesis for reinforcing and repairing a defect in a muscular or tissue wall and a method for fabricating the prosthesis that minimizes wasted mesh fabric and reduces the labor and time required for fabrication.

In one embodiment, the prosthesis includes a plug body formed of surgical mesh fabric having a closed end, a larger open end, and a cavity extending therebetween, the plug body constructed to fit within and occlude a tissue or muscle wall defect. The plug body is radially compressible upon insertion into the defect from a first configuration which is larger than the defect into a second configuration which approximates the shape of the defect. A filler body formed of the surgical mesh fabric comprising a plurality of petals extending radially outwardly from and spaced laterally about a common base is disposed in the plug body with the common base attached to the closed end of the plug body. The plug bodies are cut as circular pieces from a sheet of the mesh fabric (and, optionally, later shaped to form pleats therein) in a pattern of rows. The circular pieces in the alternate rows may be offset from each other by one half of the spacing of the circles within the rows. The filler pieces are cut from the same sheet of material as hour-glass (or dog-bone) shaped pieces from the material between adjacent circular plug body pieces so as to leave virtually no wasted material from a rectangular sheet. More specifically, one side edge of each hour-glass shaped piece is created by a cut, the other side of which cut is a segment of the circumferential edge of a circular plug body piece. The other side edge of each hour-glass shaped piece is formed by a cut, the other side of which cut is a segment of the circumferential edge of the next adjacent circular plug body piece in a row. The longitudinal ends of each filler piece may additionally be formed as one side of cuts forming segments of the circumferential edges of two other adjacent circular plug pieces in the adjacent rows.

In this manner, almost the entire sheet of mesh fabric can be used to form either a plug body piece or a filler piece, with no or very little wasted material.

According to another time and cost-saving measure, the filler pieces are attached to the plug body by welding.

DESCRIPTION OF THE PREFERRED EMBODIMENTS

Figure 3:
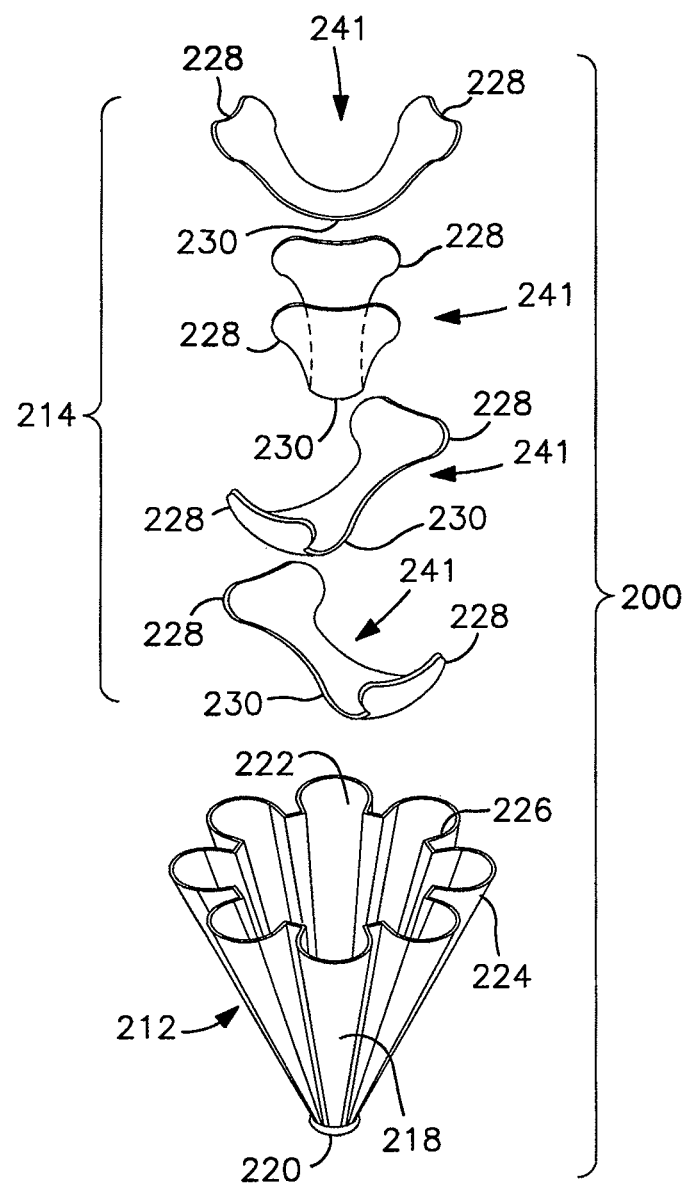
FIG. 3 is an exploded illustration of an implantable mesh prosthesis in accordance with an exemplary embodiment of the present invention.
Figure 4:
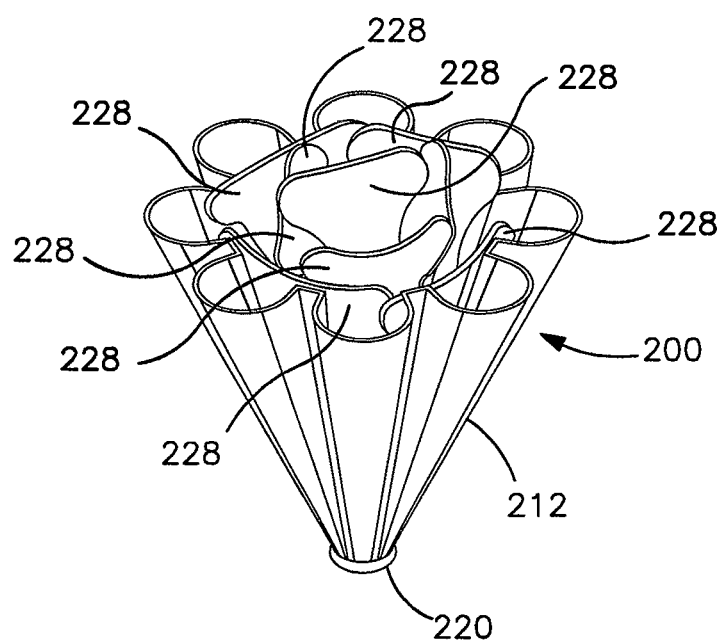
FIG. 4 is an illustration of the implantable mesh prosthesis of FIG. 2, shown assembled.

An exemplary implantable prosthesis 200 for repairing tissue and muscle wall defects in accordance with the principles of the present invention is illustrated in FIGS. 3 and 4 in exploded and assembled form, respectively. The prosthesis 200 includes a conical plug body 212 that is compressible into a slender configuration that approximates the shape of a defect, and an inner filler body 214 that imparts bulk and stiffens the prosthesis 200 when it is confined within a hernia opening. The surface of the conical plug body 212 may bear pleats 218, which enhance the flexibility and pliability of the prosthesis, allowing the prosthesis to conform to irregularities in the shape of the hernia without kinking. The tight and contiguous fit minimizes the formation of gaps between the prosthesis and the surrounding tissue, which gaps could potentially lead to recurrent herniation.

The conical plug body 212 preferably is formed by hot molding a circular piece of surgical mesh fabric into a cone. Other configurations, such as a truncated cone or a cylinder, are contemplated also. The plug body 212 has a blunt closed end 220 which minimizes injury to the surgical area when the prosthesis is implanted. The central portion of the plug body is hollow and defines a cavity 222 that may be provided with filler material that increases the bulk and stiffness of the plug body when compressed within the conical plug body 212.

Figure 1:
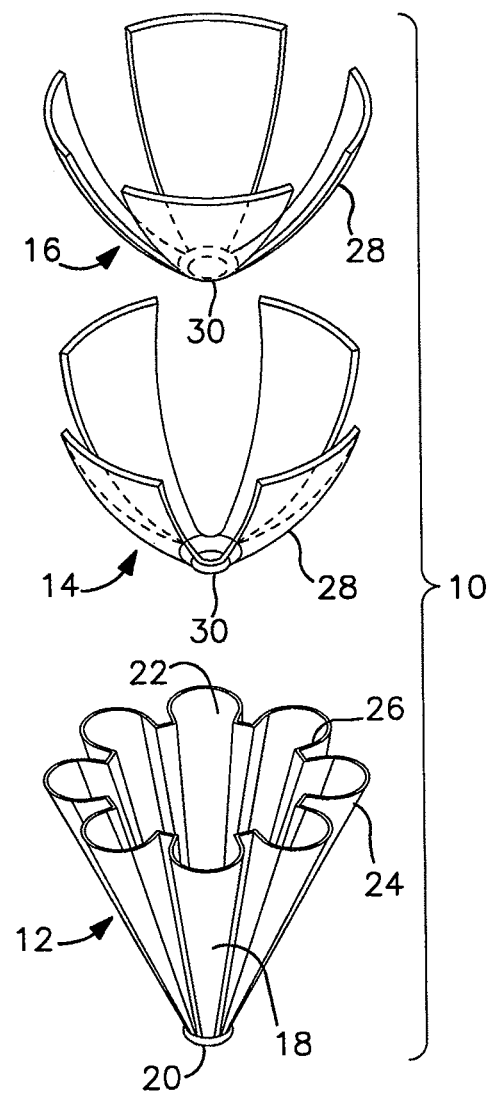
FIG. 1 is an exploded view of a prior art conical mesh prosthesis for repairing tissue walls.
Figure 2:
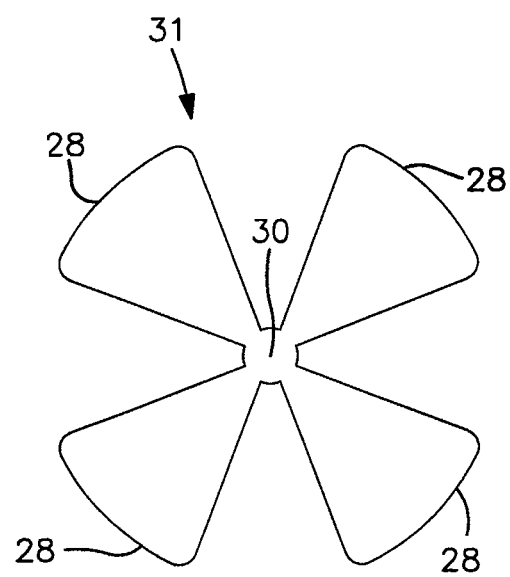
FIG. 2 is a plan view of a filler piece of mesh fabric for forming at least a part of a filler body of a prosthesis in accordance with the prior art.

Pleats 218 may be hot molded into the plug body 212 and carried on both the inner and outer surfaces of the plug body. The pleats 218 enhance the flexibility and pliability of the plug body 212, allowing the cone to conform to various irregularities in the contour of the tissue defect. The pleats 218 illustrated in FIGS. 2 and 3 are formed by alternating rounded peaks 224 and pointed valleys 226, similar in appearance to a corrugated surface, which taper inwardly towards the closed end 220 of the plug body 212. Other pleat configurations also may be used as long as the pleat allows the plug body to closely conform to an irregular defect contour. The pleats 218 preferably are provided about the entire surface of the plug body 212 so that any portion of the cone has the ability to conform to a localized irregularity in the tissue or muscle structure defining the defect. Alternatively, the pleats may be provided on only that limited portion of the plug body that is likely to encounter the irregular topography or that will require enhanced flexibility.

The conical prosthesis may be provided with a mesh inner filler body 214 that stiffens and packs the prosthesis 200 when it is compressed within the defect. The inner filler body 214 consists of a plurality of mesh filler pieces 241 that can best be described as dog-bone shaped, each dog-bone shaped filler piece 241 comprising two petals 228 that extend radially outwardly and upwardly from a central base 230 into the hollow cavity 222 of the plug body 212. In an assembled form, the bases 230 are attached to the closed end 220 of the plug body 212. The petals 228 may be rounded, as illustrated. Other configurations of mesh filler are contemplated also.

The plug body 212 and the filler body 214 may be joined together by suturing the common base 230 of the filler body 214 to the closed end 220 of the plug body 212. Likewise, two or more of the filler pieces may be joined together by suturing. In fact, two or more filler pieces 231 and the plug body 220 all may be sutured together at one time with the same suture(s). Other means of attachment may be utilized, for example by bonding or stapling the mesh pieces together.

The flexible petals 228 preferably spread outwardly against the inner surface of the plug body 212, packing and stiffening the prosthesis 200 when it is compressed.

Using the internal filler body 214 to impart rigidity to the prosthesis 200, rather than stiffening the plug body 212 itself, reduces the likelihood that the prosthesis 200 will kink or buckle when compressed into an irregular opening. Providing filler in the center of the prosthesis also eliminates regions of dead or open space which may weaken the prosthetic repair.

Figure 5:
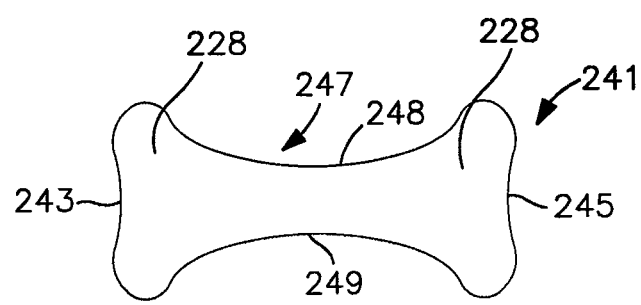
FIG. 5 is a plan view of a filler piece of mesh fabric for forming at least a part of a filler body of a prosthesis in accordance with an exemplary embodiment of the present invention.
Figure 6:
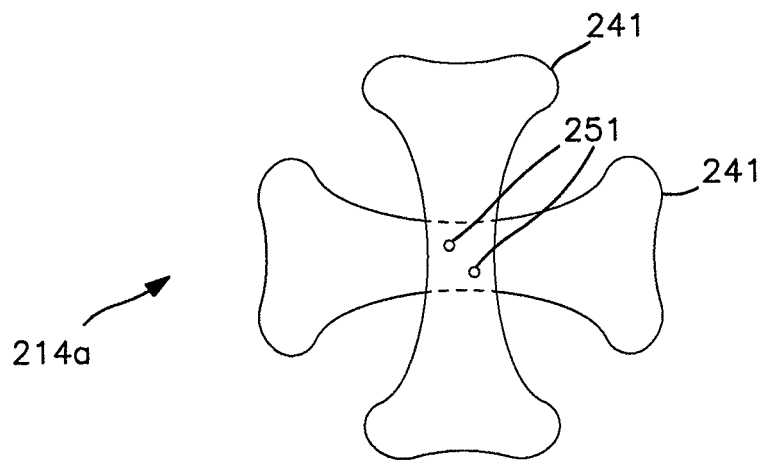
FIG. 6 shows two of the filler pieces of FIG. 5 joined together to form a prosthesis filler body having four radially-spaced petals.
Figure 7:
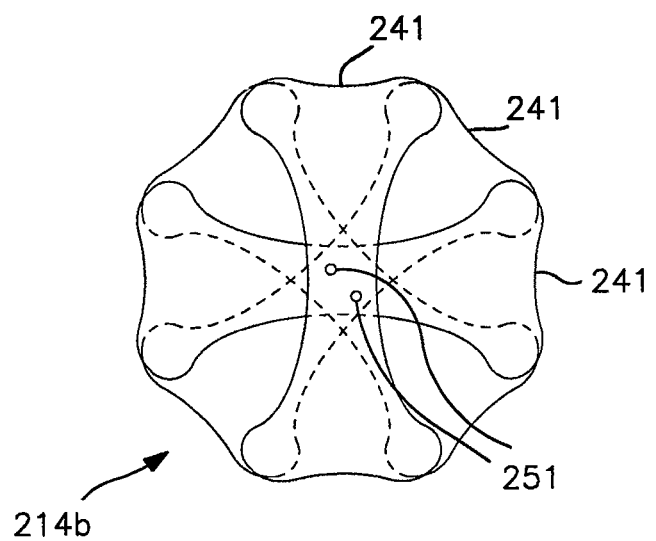
FIG. 7 shows four of the filler pieces of FIG. 5 joined together to form a prosthesis filler body having eight radially-spaced petals.

Recently, newer surgical mesh fabrics have been developed that have superior properties for repairing hernias and the like that are suitable for fabricating the prostheses of the kind discussed herein. Generally, these newer mesh materials are more expensive than earlier surgical mesh fabrics. Due to their increased expense, it is desirable to use as much of the sheet of material as possible by minimizing wasted material cut from the rectangular sheets to form the plug bodies and filler bodies. Accordingly, the filler bodies 214 are formed in a shape that minimizes waste, as will be described in more detail in connection with FIGS. 5-10. FIGS. 5, 6, and 7 illustrate a form for the filler body (these alternate forms also are the forms shown in the embodiments of FIGS. 2 and 3).

Referring first to FIG. 5, in one embodiment, the filler bodies 214 are formed from one or more pieces 241 of mesh material such as that illustrated in FIG. 5. As can be seen, filler mesh fabric piece 241 is generally shaped like a dog-bone. Alternately, it might be described as hourglass shaped. The filler piece 241 has first and second longitudinal ends 243, 245 that are wider than the intermediate longitudinal segment 247 that joins the two ends 243, 245. The intermediate segment 247 defines two opposing side edges 248, 249 that are arcuate in shape and mutually diverging (i.e., the insides of the arcs face away from each other to form a concave profile), giving the piece 241 the aforementioned overall dog-bone or hourglass shape. The first and second ends 243, 245 will each form one of the petals 228 of the filler body. Specifically, as illustrated in FIG. 6, two of the filler pieces 241 can be stacked on top of each other radially rotationally offset 90° relative to each other and joined in their middles to form a filler body 214a having four radially spaced petals 228. Any number of such pieces 241 may be stacked to form a filler body having any even number of petals radially extending from a common central base. For instance, three such filler pieces may be joined together rotationally offset from each other by 60° to form a filler body having six evenly radially-spaced petals 228. In one preferred embodiment illustrated in FIG. 7, four such filler pieces 241 are joined together rotationally offset from each other by 45° to form a filler body 214b having eight evenly radially-spaced petals 228.

The filler pieces 241 may be joined to each other (and the filler pieces may be further joined to the closed end of the plug body piece 220) by any reasonable means such as the aforementioned suturing or adhesive bonding. However, in one preferred embodiment, the filler pieces 241 and plug body piece 220 are welded to each other, such as by ultrasonic welding. By melting the layers of mesh material and allowing them to re-solidify while they are in contact, the various pieces 241, 220 can be joined to each other. In one embodiment, the pieces are spot welded to each other at their centers with one or two spot welds 251, as shown in FIGS. 6 and 7.

Figure 8:
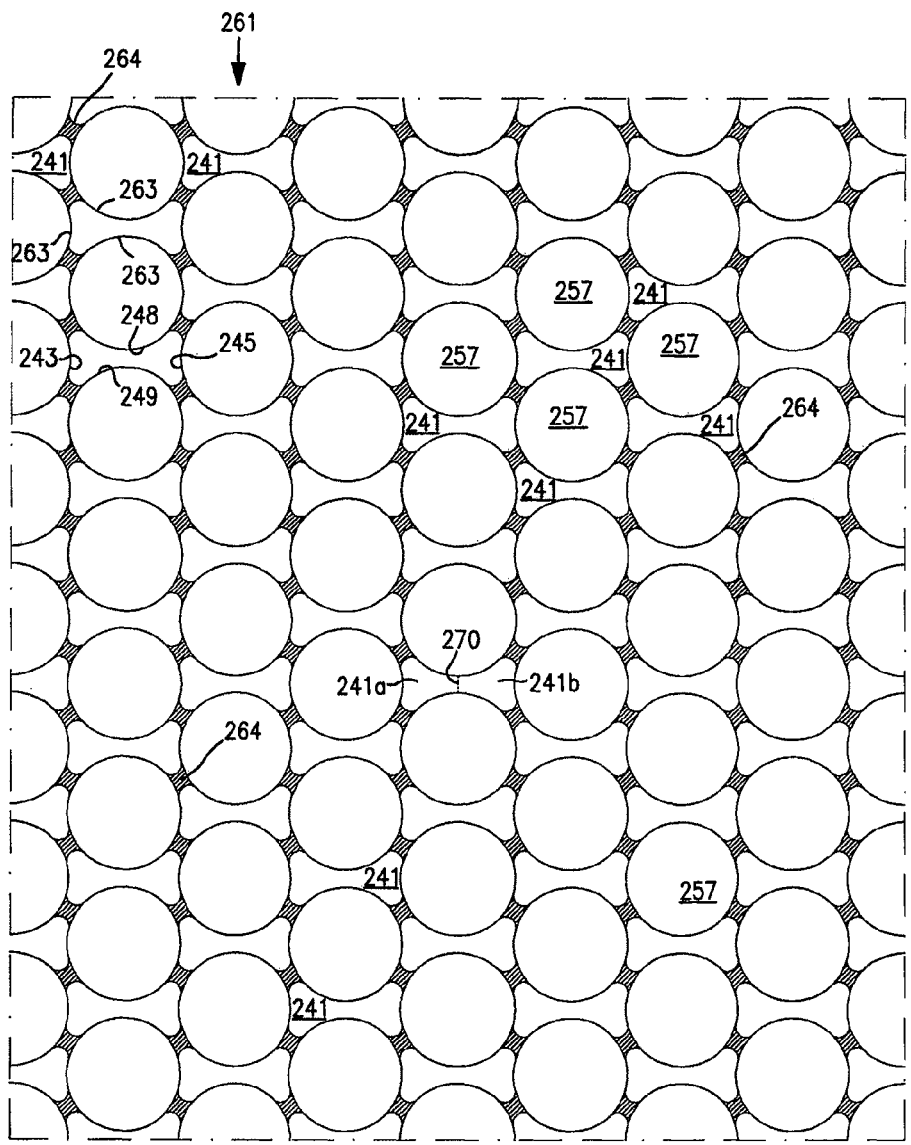
FIG. 8 is a plan view of a sheet of mesh fabric showing a pattern for cutting pieces for forming the plug bodies and filler bodies of the prosthesis of FIGS. 3 and 4.

The dog-bone shaped filler pieces 241 have a significant advantage over the prior art pieces of FIG. 2. Specifically, a plurality of the filler pieces 241 and a plurality of the plug body pieces can be cut from a square or rectangular sheet of mesh material in a pattern that wastes almost none of the material of the sheet. One such pattern is illustrated in FIG. 8. As can be seen, the sheet of material 255 is cut into a plurality of circular pieces 257 arranged in rows 261, with the adjacent rows offset from each other by one half of the center-to-center spacing, s, of the circles 257 in a row. These circular pieces 257 will be used to form the conical plug bodies 212. The filler pieces 241 are formed from the material between each adjacent circular piece 257 in each row 261. As can be seen, the arcuate side edges 248, 249 of each filler piece 241 is contiguous with and formed by the same cut that forms a segment of the circumferential edge of one of the circular plug body pieces 220. That is, one side of the cut forms a side edge 248, 249 of a filler piece 241 while the other side of the cut forms part of the circumferential edge of a circular plug body piece 220.

As shown, the longitudinal end edges 245, 247 of each filler pieces 241 also may be arcuate and contiguous with and formed by the same cut as a segment of the circumferential edges of the circular plug pieces 257 in the adjacent, offset rows on either side of the row the filler piece is in.

Thus, each circular plug piece 257 is surrounded by and separated from the adjacent circular plug body piece 257 in each of four orthogonal directions by a different filler piece 241. The arcs of the side edges of the filler pieces 247 will have the same radius as the circular pieces 257. The arcs of the longitudinal ends 245, 247 of the filler pieces also will have the same radius in the embodiment of FIG. 8.

In the embodiment illustrated in FIG. 8, the only discarded material is in the regions 263. However, even those regions 263 can be made smaller or entirely eliminated depending on how wide and how long one wishes the petals 228 to be. For example, the corners 265 of the petals may be made contiguous with the corners 265 of the adjacent petals as illustrated in FIG. 9, such that there is no discarded material at all.

Figure 9:
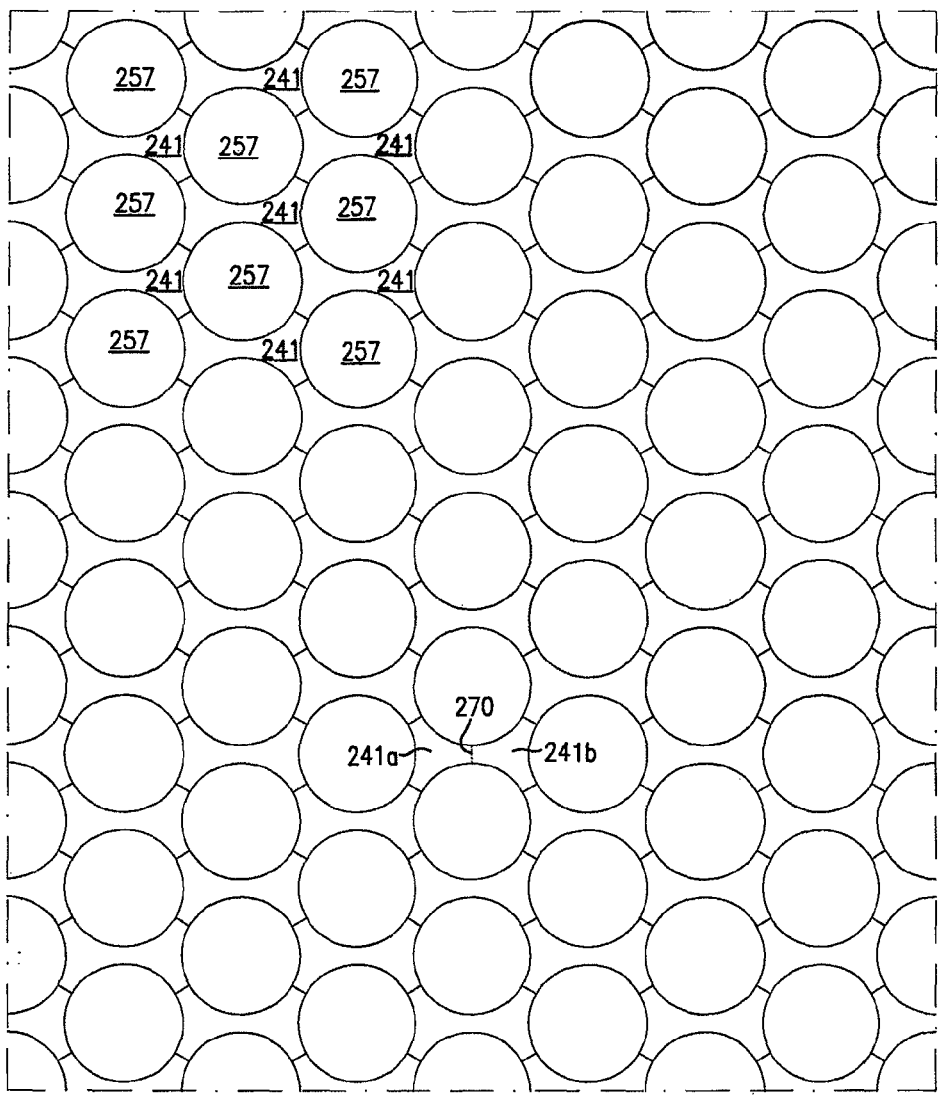
FIG. 9 is a plan view of a sheet of mesh fabric showing an alternate pattern for cutting pieces for forming the plug bodies and filler bodies of the prosthesis of FIGS. 3 and 4, with no wasted material.

As noted, in the embodiments of FIGS. 8 and 9, the side edges 248, 249 of the filler pieces are contiguous with a portion of the circumferential edges of the circular plug body pieces 257. That is, the side edges 248, 249 are formed by one side of a cut, the other side of which cut forms a portion of the circumferential edge 265 of one of the circular plug body pieces 257. Note, for instance, that, in the FIG. 8 embodiment, one side edge 248 of each of the filler pieces 241 is contiguous with almost a 90° segment of the circumferential edge of circular plug body piece 257 below it in its row and the other side edge 249 of each of the filler pieces 241 is contiguous with almost a 90° segment of the circular plug body piece 257 above it in its row. Note that, in this embodiment, the longitudinal end edges 243 and 245 of the filler pieces 241 also are contiguous with an arcuate segment 263 (about 30° in the FIG. 8 embodiment) of the adjacent circular plug body pieces 257 in the adjacent rows.

Figure 10:
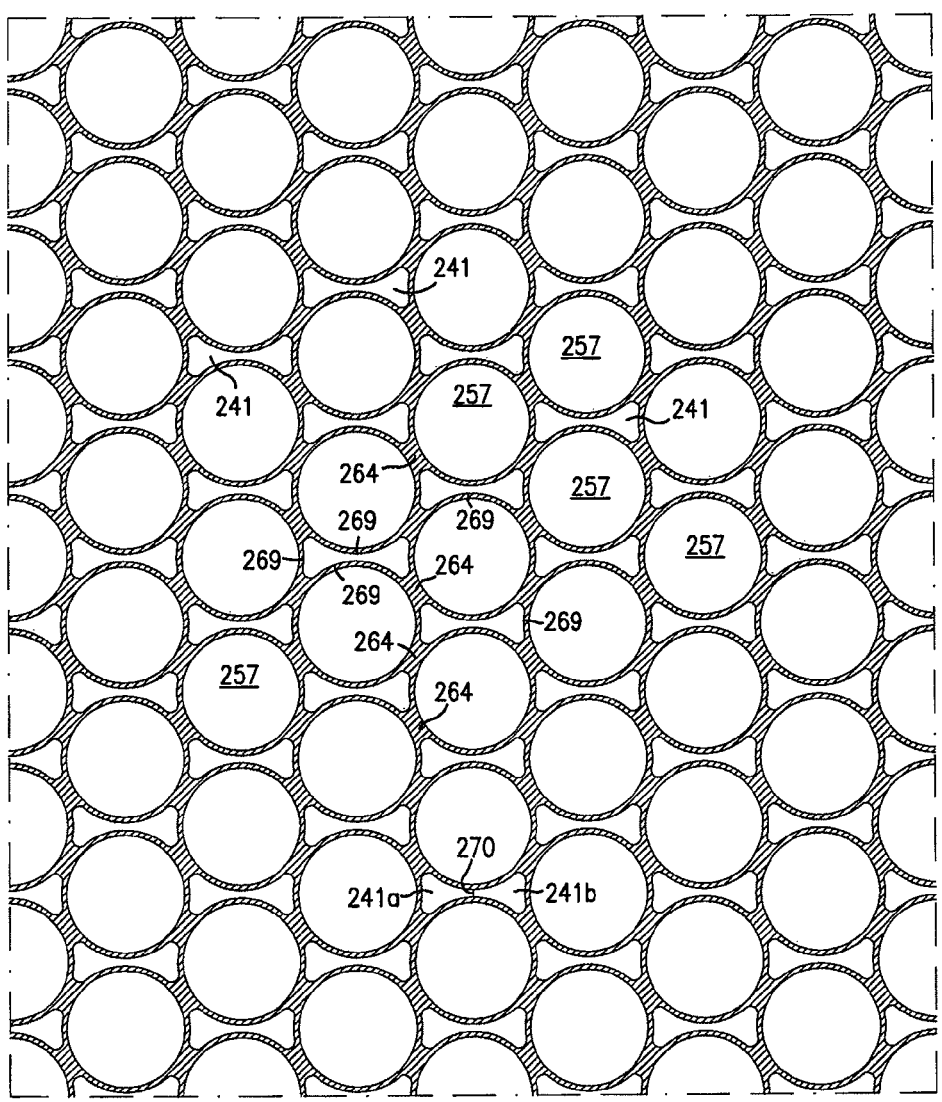
FIG. 10 is a plan view of a sheet of mesh fabric showing yet another alternate pattern for cutting pieces for forming the plug bodies and filler bodies for the prosthesis.

On the other hand, the various edge portions 243, 245, 248, 249 of the filler pieces 241 and the adjacent circumferential edges segments 263 of the circular plug body pieces 257 do not have to be contiguous with each other (e.g., formed by the same cut). If, for any reason, it is desired that the filler pieces 241 be shorter or less wide relative to the circular plug body pieces 257 than in the embodiment of FIG. 8, then they may be cut as such, as illustrated in FIG. 10. In such a case, there will be slightly more wasted material (in the form of thin arcuate strips of material 269 between the filler pieces 241 and the circular plug body pieces 257 joining the waste regions 264 to each other).

Figure 11:
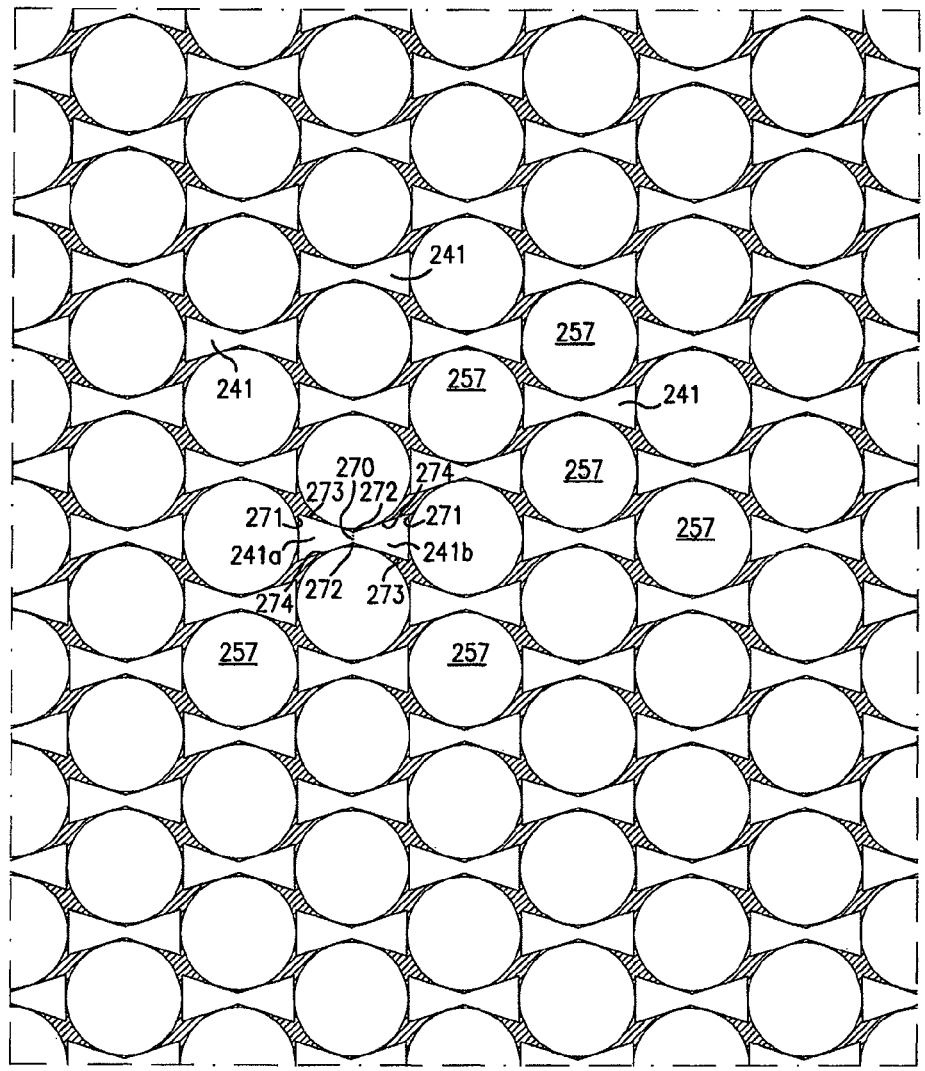
FIG. 11 is a plan view of a sheet of mesh fabric showing yet another alternate pattern for cutting pieces for forming the plug bodies and filler bodies for the prosthesis.

In yet other embodiments, the filler pieces need not have arcuate side edges, but may have straight side edges to form a bow-tie type shape, such as the filler piece 241 illustrated in FIG. 11. The use of filler pieces with straight side edges will result in slightly more wasted material. However, the filler pieces 241 still can be cut from the material between the circular plug body pieces 257 while utilizing most of the material in those spaces, as seen in FIG. 11.

The dog-bone, bow-tie, or other shaped filler pieces 241 as shown in FIGS. 8 through 11, of course, do not necessarily have to be cut as single pieces as shown, but may be cut as two (or more) pieces. For instance, it is envisioned that, depending upon the technique for assembling the final plug product, the desired filler pattern for providing suitable stiffness to the plug, and/or the desired number of petals, it may be desirable to form each petal individually by, for instance, adding a cut transversely across the middle of the bow-tie shape, such as illustrated by the dashed lines 270 in FIGS. 8-11 to form two filler pieces 241a and 241b, each for forming a single petal of the filler body.

Each of these filler pieces 241a, 241b may be described as comprising first and second longitudinal ends 271, 272 and substantially longitudinal opposing side edges 273, 274 therebetween, the first end 271 being wider than the second end 272. The first and second side edges 273, 274 converge toward each other from the first longitudinal end 271 toward the second longitudinal end 272. A pair of these filler pieces 241a and 241b are formed from each piece of the surgical mesh material located between adjacent circular plug body pieces, with the second longitudinal ends 272 of the filler body pieces of each pair facing each other.

The plug filler bodies can be formed by welding, sewing, adhering or otherwise attaching the smaller, second ends of the filler pieces 241a, 241b to the plug body pieces, with the larger, second ends forming the petals.

Figure 12:
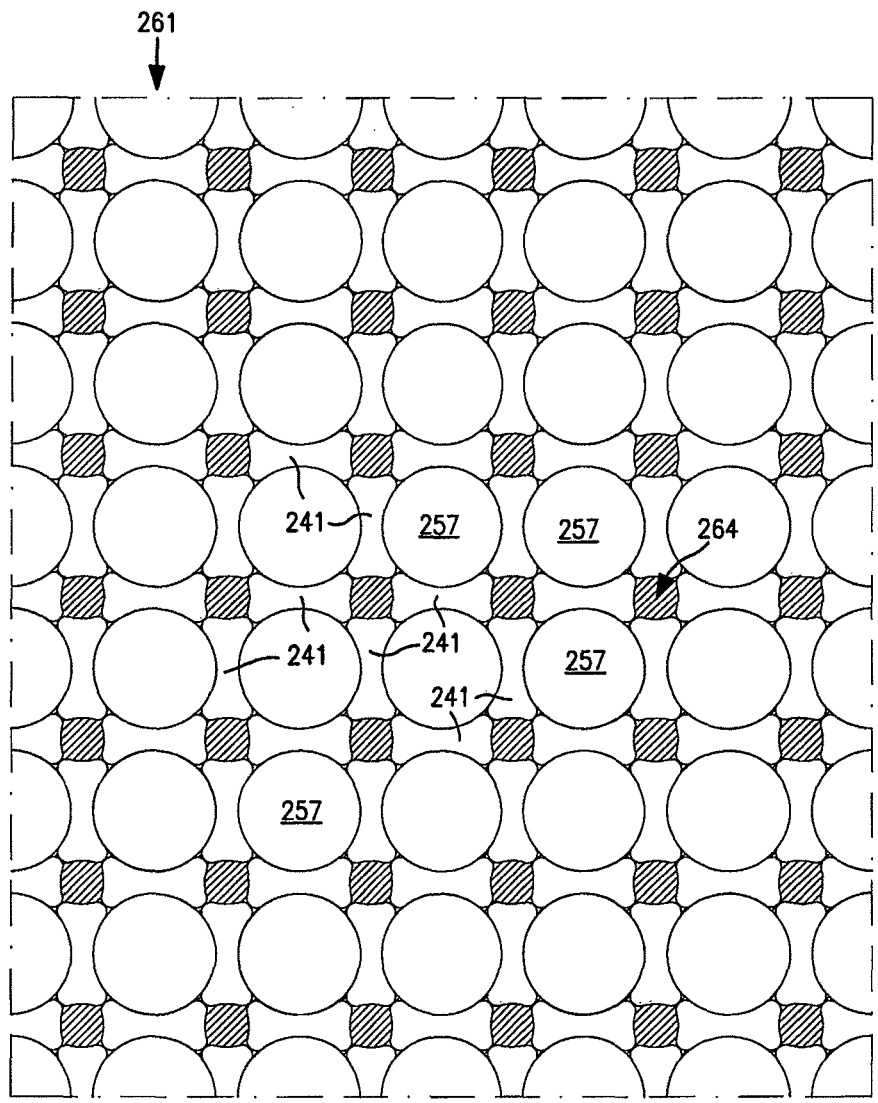
FIG. 12 is a plan view of a sheet of mesh fabric showing yet one more alternate pattern for cutting pieces for forming the plug bodies and filler bodies for the prosthesis.

FIG. 12 illustrates yet another pattern for cutting the filler pieces 241 and body pieces 257. Particularly, in this embodiment, the circular body pieces 257 in all of the rows 261 are even with each other (i.e., not offset by half of the circle to circle spacing as in the embodiments of FIGS. 8, 9, 10, and 11). In this pattern, the dog-bone shaped filler pieces 241 in the rows are oriented with their longitudinal axes transversely across the rows (just as in FIGS. 8-11), but the dog-bone shaped filler pieces 241 between the rows 261 are oriented with their longitudinal axes parallel to the rows. The wasted material 264 areas are in a different location relative to the embodiment of FIG. 8, for instance, but comprises roughly the same amount of material for roughly the same dimension filler and body pieces.

The sheet of mesh material may be cut by die cutting, laser cutting, or any other reasonable cutting means.

Figure 13:
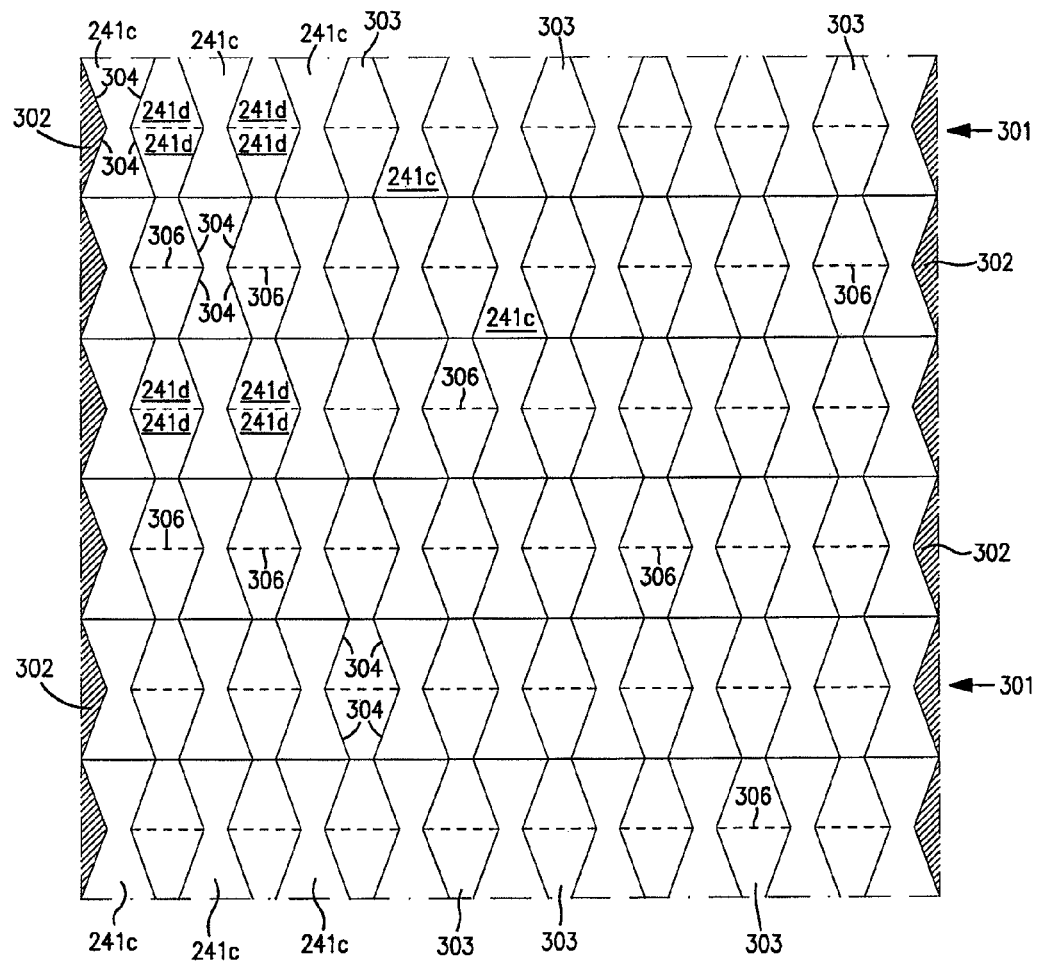
FIG. 13 is a plan view of a sheet of mesh fabric showing yet one more alternate pattern for cutting pieces for forming the filler bodies for the prosthesis.
Figure 14:
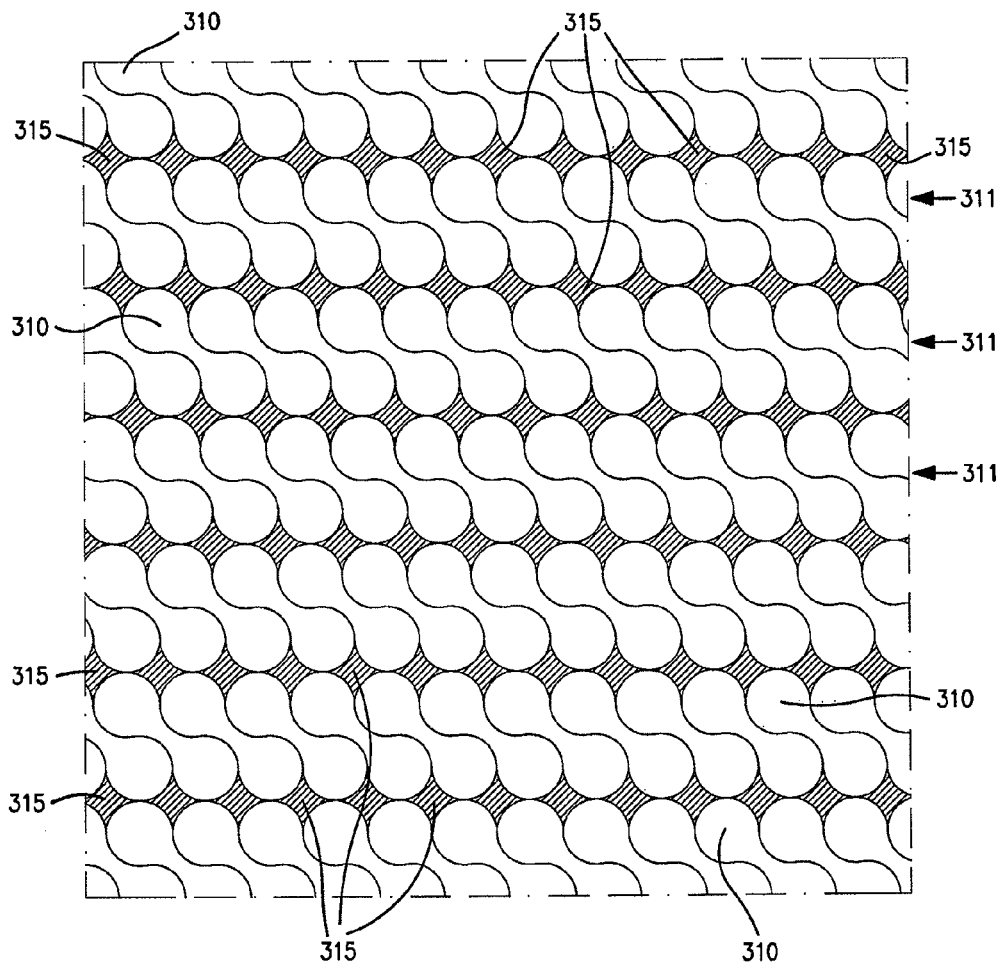
FIG. 14 is a plan view of a sheet of mesh fabric showing another alternate pattern for cutting pieces for forming the filler bodies for the prosthesis.

FIGS. 13 and 14 illustrate yet further alternate embodiments of techniques for cutting the filler pieces 241 from a sheet of surgical mesh. In these embodiments, the filler pieces 241 are cut from sheets separately from the circular pieces 257 for forming the conical bodies 12. This does not necessarily mean that they are cut from separate sheets, but merely that the filler pieces 241 are not interleaved with the body pieces 257 in the intimate way of the previously discussed embodiments.

Referring first to the embodiment of FIG. 13, filler pieces similar or identical to the bow-tie filler pieces described above in connection with FIG. 11 are formed in rows 301 from a surgical mesh sheet as shown. This technique leaves essentially no wasted material from forming the filler pieces, except possibly for a small triangular piece 302 at each end of each row. There is no wasted material between the rows 301. Within each row 301, a plurality of single-piece bow-tie type filler pieces 241c are formed by severing at solid lines 304, as shown. The pieces of material 303 left between each pair of adjacent bow-tie filler pieces 241c can be cut along dashed lines 306 to form two half bow-tie pieces 241d. Any two half pieces 241d can be sewn or welded together at their wider ends (i.e., the end at cut 306) to form a full bow-tie piece, such as any of pieces 241c.

FIG. 14 shows a technique for forming the dog bone shaped filler pieces such as in the embodiments of any of FIGS. 8, 10, and 12 in rows somewhat similarly to the formation of the bow-tie shaped filler pieces as in FIG. 13. In this embodiment, dog bone shaped filler pieces 310 are formed in rows 311 as shown. The only wasted material comprises small pieces 315 between the filler pieces 310 and possibly a larger wasted piece (not shown) at each end of each row. On the other hand, the ends of the filler pieces 310 could be altered slightly so as to completely eliminate the waste pieces 315 between the filler pieces, if desired.

The mesh material should be a tissue infiltratable material that allows sufficient tissue ingrowth to secure the prosthesis to healthy tissue surrounding the defect site. The material may be a knitted monofilament mesh fabric. Alternately, the mesh may be fabricated of one or more biologic materials, such as porcine materials. Also, bioabsorbable or resorbable materials may be used. In other embodiments, parts of the mesh material may be bioabsorbable or resorbable, while other parts are nonabsorbable, including hybrid materials, and co-knitted meshes of two or more different materials. When implanted, the mesh stimulates an inflammatory reaction which promotes rapid tissue ingrowth into and around the mesh structure. Alternatively, other surgical materials which are suitable for tissue reinforcement and defect closure may be utilized, including Marlex®, Prolene®, Dacron®, Teflon® and Merselene®. It also is contemplated that the mesh fabric may be formed from multifilament yarns and that woven, molded and other recognized methods of forming prosthetic mesh materials would be suitable. Other tissue wall reinforcement materials also may be used as would be apparent to those of skill in the art.

In a representative procedure, after the sheet of mesh material is cut or otherwise sectioned into the circular plug body pieces 257 and the filler pieces 241, a plug body piece 257 is formed into a conical shape by hot molding the circular plug body piece 257 into a cone configuration. The cone is then placed in a fixture having fins that project into the mesh fabric forming rounded pleats. The plug body piece 257 is baked and then allowed to cool resulting in a hot molded plug body with the desired pleated surface. The filler bodies are formed by joining two or more of the filler pieces at their centers with the pieces preferably radially rotationally offset from each other as previously described.

The filler pieces 241 are then inserted into the conical plug body 212 so that the centers of the filler pieces seat against the closed end 220 of the plug body 212 and the petals 228 extend radially outwardly and upwardly in the direction of the open end of the plug body 212. The filler pieces may be attached to each other and/or to the conical plug body, for instance, by suturing, adhesive bonding, or welding. Welding is a preferred method of joining the various pieces together because it is much less labor and time intensive and requires fewer materials than suturing and adhesive bonding (no sutures and no adhesive).

Figure 15:
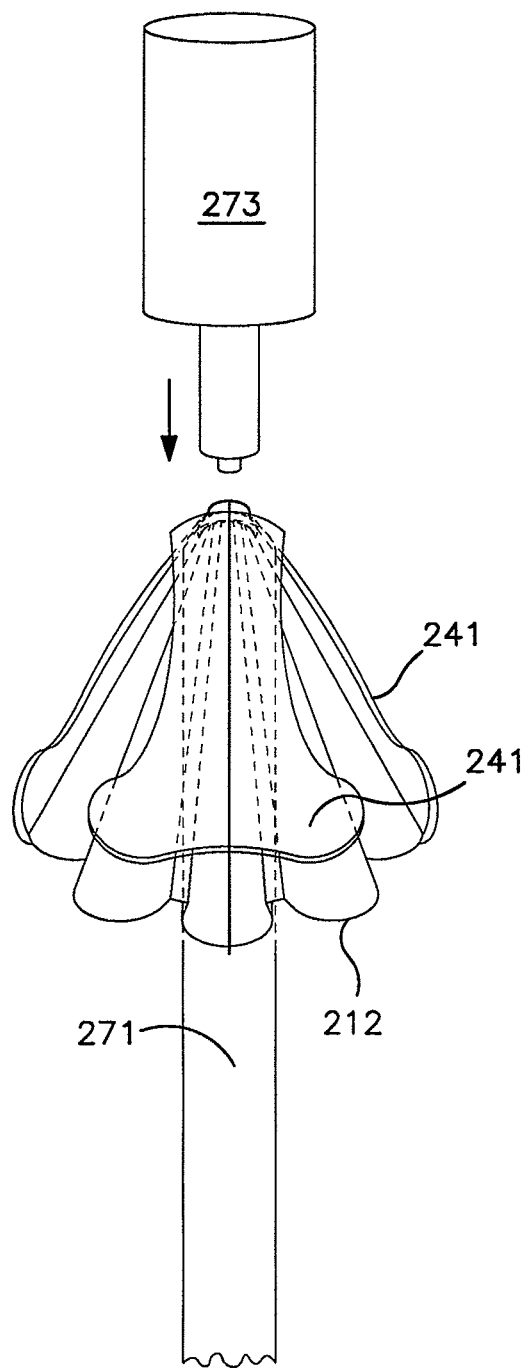
FIG. 15 is a diagram illustrating an exemplary apparatus and process for welding the filler pieces to the plug body piece to form a prosthesis in accordance with the principles of the present invention.

FIG. 15 helps illustrate one technique for welding the filler pieces 241 and the plug body 212 together to form a prosthesis 200. In this technique, the conical plug body 212 is inverted so that it is inside out. It is then placed on a stainless steel mandrel 271. A plurality of filler pieces 241 (each comprising two petals 228) are placed on top of the conical plug body 212 as shown. FIG. 15 illustrates two such filler pieces 241 in order to keep the drawing relatively simple. However, as previously noted, one, three, four, or more filler pieces 241 may be incorporated. A hold-down tool (not shown) may be used to hold the four filler pieces 241 and the plug body 212 together, if desired. Then, an ultrasonic welding tip 273 comes down on top of the mandrel 271 to form spot welds that weld the layers together. Two or more spot welds may be made, if desired.

The prosthesis may be subject to a final heat treatment to set the cone and filler pieces in the desired configuration. The resulting prosthesis includes a hot molded conical plug body 212 with a pleated surface formed from a plug body piece 257 that conforms to the varying contour of a defect and a filler body 214 formed of one or more of the filler pieces 241, which filler body stiffens the prosthesis when it is compressed in the narrow defect.

The pleated conical plug prosthesis is extremely pliable, allowing localized portions of the prosthesis to adapt to any irregular contours of the defect. The surface of the implanted conical plug prosthesis is substantially flush with the tissue surrounding the defect, providing a contiguous and tight fit that, is believed to improve the likelihood of a permanent, non-recurrent repair.

In a representative inguinal hernia repair, the hernia region is reached by an anterior surgical approach. For indirect hernias, the lipoma of the cord and the sac are dissected free. The prosthesis is inserted through the internal ring, closed end 220 first, and positioned just beneath the crura. For direct hernias, the defect is circumscribed at its base and the contents fully reduced. The conical mesh prosthesis 200 is then inserted through the opening until the closed end 220 lies flush with or slightly beyond the margin of the defect. The compressed prosthesis conforms to the defect shape, providing a snug fit within the abdominal wall defect.

The stiffness of the compressed plug prosthesis may be adjusted by snipping off individual petals 228 of the inner filler body 214 if the surgeon determines that the prosthesis otherwise will become too tightly packed. Depending upon the type of hernia being repaired and the practice of the surgeon, the conical plug body 212 and, or alternatively, individual petals 228 of the filler body 214, may be sutured to surrounding tissue. Each of the petals 228 may be sutured or otherwise joined to neighboring tissue after implantation without drawing the entire filler body 214 toward the suture site, reducing the likelihood of overpacking a portion of the prosthesis which potentially could lead to recurrent herniation. A separate flat mesh overlay may be placed over the closed end 220 of the conical prosthesis to reinforce the internal ring and the inguinal canal. The overlay may be shaped to match the configuration of the inguinal canal. A slit is spreadable to allow positioning of the spermatic cord in the centered hole. The slit section is then sutured together, preferably using a nonabsorbable monofilament thread, providing a prosthetic reinforcement of the inguinal canal and the internal ring. Within a short period of time, fibroblastic proliferation and collagen formation will penetrate the mesh, securely anchoring the prosthesis in place.

The composite of the present invention is particularly indicated for repair of abdominal wall defects such as inguinal (direct and indirect), femoral, incisional and recurrent hernias. It also is contemplated that the implantable prosthesis would have applications in laparoscopic procedures.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An implantable prosthesis for repairing a tissue or muscle wall comprising:
a plug body of surgical mesh material, the plug body including a closed end, an open end larger than the closed end, and a cavity extending therebetween, the plug body being constructed and arranged to fit within and occlude a defect in the tissue or muscle wall; and
a filler body of surgical mesh material, the filler body comprising a plurality of petals extending radially outwardly from a common base and being spaced laterally thereabout, the filler body being disposed within the cavity with the common base attached to the closed end of the plug body;
wherein at least two of the petals are shaped as a longitudinal strip having first and second longitudinal ends and substantially longitudinal opposing side edges, the first and second longitudinal ends being wider than a longitudinal segment intermediate the first and second longitudinal ends, the first and second longitudinal ends each comprising one of the petals; and
wherein the plug body has a convex peripheral edge complementary to a concave peripheral edge of the filler body.

2. The prosthesis of claim 1 wherein the opposing side edges of the longitudinal strip are arcuate and diverging.

3. The prosthesis of claim 2 wherein the longitudinal strip is substantially dog-bone shaped.

4. The prosthesis of claim 2 wherein the side edges are substantially segments of a circle.

5. The prosthesis of claim 4 wherein the plug body is formed from a substantially flat and substantially circular piece of surgical mesh material of a radius, and wherein the first and second side edges of the petals have substantially the same radius as the radius of the substantially circular piece.

6. The prosthesis of claim 5 wherein the plug body and the longitudinal strips are formed from a single sheet of the surgical mesh material.

7. The prosthesis of claim 2 wherein the common base is welded to the closed end of the plug body.

8. The prosthesis of claim 1 wherein the filler body comprises a plurality of longitudinal strips stacked and radially rotationally offset from each other.

9. The prosthesis of claim 8 wherein the plurality of longitudinal strips comprises at least two stacked first pieces radially rotationally offset from each other by approximately 90°.

10. An implantable prosthesis for repairing a tissue or muscle wall comprising:
a plug body of surgical mesh material, the plug body including a closed end, an open end larger than the closed end, and a cavity extending therebetween, the plug body being constructed and arranged to fit within and occlude a defect in the tissue or muscle wall; and
a filler body comprising a plurality of filler pieces of surgical mesh material, the filler body comprising a plurality of petals extending radially outwardly from a common base and being spaced laterally thereabout, the common base being attached to the closed end of the plug body;
wherein at least two of the petals are formed in the shape of a longitudinal strip having first and second longitudinal ends and substantially longitudinal opposing side edges, the first and second longitudinal ends being wider than a longitudinal segment intermediate the first and second longitudinal ends, the first and second longitudinal ends each comprising one of the petals; and
wherein the plug body has a peripheral edge portion complementary to a respective peripheral edge portion of the entire longitudinal segment of each longitudinal strip.

11. The prosthesis of claim 10 wherein the plug body is formed from a substantially flat and substantially circular piece of surgical mesh material of a radius, and wherein the first and second side edges of the petals have substantially the same radius as the radius of the substantially circular piece.

12. The prosthesis of claim 11 wherein each of the first and second longitudinal ends has a curved edge having substantially the same radius as the radius of the substantially circular piece.

13. The prosthesis of claim 11 wherein the plug body and the longitudinal strips are formed from a single sheet of the surgical mesh material.

14. The prosthesis of claim 10 the longitudinal strips have a shape complementary to a respective shape of the plug body.

15. The prosthesis of claim 10 wherein each of the first and second longitudinal ends has an end edge having a shape complementary to a respective shape of the plug body.

16. An implantable prosthesis for repairing a tissue or muscle wall comprising:
a plug body cut from a flat sheet of surgical mesh material, the plug body including a closed end, an open end larger than the closed end, and a cavity extending therebetween, the plug body being constructed and arranged to fit within and occlude a defect in the tissue or muscle wall; and
a filler body comprising a plurality of filler pieces, each of the plurality of filler pieces being cut from the flat sheet of surgical mesh material, the filler body comprising a plurality of petals extending radially outwardly from a common base and being spaced laterally thereabout, the common base being attached to the closed end of the plug body;
wherein at least two of the petals are formed of a first piece of flat surgical mesh material in the shape of a longitudinal strip having first and second longitudinal ends and substantially longitudinal opposing side edges, the first and second longitudinal ends being wider than a longitudinal segment intermediate the first and second longitudinal ends, the first and second longitudinal ends each comprising one of the petals; and wherein the plug body is formed of a second piece of flat surgical mesh material, and wherein the first and second side edges of the first piece of flat surgical mesh material have a segment having a shape complementary to a respective shape of a respective segment of the second piece of flat surgical mesh material, so that the first piece and the second piece may be laid out in closely-spaced adjacent relationship with the respective segments of the first and second pieces nested within one another, and be cut from, a single sheet of flat surgical mesh material.

17. The prosthesis of claim 16 wherein each of the first and second longitudinal ends has an end edge having a shape complementary to a respective shape of the second piece of surgical mesh material.

18. The prosthesis of claim 16 wherein the second piece of surgical mesh material has a substantially circular shape of a radius, and wherein the first and second side edges of the first piece of surgical mesh material have substantially the same radius as the radius of the second piece of surgical mesh material.

19. The prosthesis of claim 16 wherein the second piece of surgical mesh material has a substantially circular shape of a radius, and wherein each of the end edges has substantially the same radius as the radius of the second piece of surgical mesh material.

20. The prosthesis of claim 16 wherein the second piece of surgical mesh material has a substantially circular shape of a radius, and wherein each of the first and second side edges of the first piece of surgical mesh material and each of the end edges has substantially the same radius as the radius of the second piece of surgical mesh material.

* * * * *